United States Patent [19]
DeFina

[11] Patent Number: 5,614,202
[45] Date of Patent: Mar. 25, 1997

[54] MOISTURIZING GLOVE

[76] Inventor: Linda E. DeFina, 5830 Alderleaf Pl., Columbia, Md. 21045

[21] Appl. No.: 243,833

[22] Filed: May 17, 1994

[51] Int. Cl.$^6$ .................................................. A61F 13/00
[52] U.S. Cl. ............................................. 424/402; 424/400
[58] Field of Search .................................. 424/402, 400

[56] References Cited

U.S. PATENT DOCUMENTS

| | | | |
|---|---|---|---|
| 2,501,565 | 3/1950 | Halley | 128/165 |
| 2,916,036 | 12/1959 | Sutton | 128/260 |
| 3,116,732 | 1/1964 | Cahill | 128/260 |
| 3,896,807 | 7/1975 | Buchalter | 128/261 |
| 4,951,815 | 8/1990 | Ulbrich | 206/213 |

Primary Examiner—Thurman K. Page
Assistant Examiner—Sharon Howard
Attorney, Agent, or Firm—Robert E. Bushnell, Esq.

[57] ABSTRACT

A moisturizing glove is disclosed in which a middle layer saturated with lotion, an exterior layer of non-porous material formed to the top side of the middle layer, and an inner layer having a plurality of pores, formed to the bottom side of the middle layer create a cavity for receiving and enveloping a human extremity, particularly a human hand.

22 Claims, 3 Drawing Sheets

MOISTURIZING GLOVE

BACKGROUND OF THE INVENTION

1. Field of the Invention

The present invention relates to improvements in hand moisturizing devices and methods, and more particularly, to apparel for applying various types of skin care medications and lotions to human extremities over an extended period of time.

2. Description of the Background Art

Traditional skin care techniques associated with soothing and healing dry, itching or otherwise damaged skin are primitive. According to traditional methods, one who wishes to soothe or heal dry, itching or otherwise damaged skin applies a moisturizing lotion or a medicated lotion directly to an affected area of the body. The lotion is absorbed by the skin as it begins to treat the affected area. To continue treatment, the user must re-apply additional lotion to the affected area after the lotion is completely absorbed.

Pre-lubricated gloves are most commonly designed for medical use. Generally, pre-lubricated gloves consist of a form-fitting glove with a pre-existing lubricating material disposed on the outer surface or the inner surface of the glove. Lubricating material disposed on the inner surface of the glove reduces friction between the glove and the hand of a user, thereby enabling easy application and removal of the glove. Lubricating material disposed on the outer surface of the glove reduces friction between the glove and the surface of an external object. Consequently, pre-lubricated gloves are utilized in many medical applications.

Standard surgical gloves made of rubber or latex are commonly lined with lubricating powders such as talc, to reduce friction between the hand of a surgeon and the surgical glove, thereby enabling easy application and removal of the glove. Similarly, Podell, Jr. et al. (U.S. Pat. No. 3,813,695) discloses a surgical glove laminated with an internal plastic lining of hydrophilic material. The hydrophilic lining reduces friction between the glove and the hand of the surgeon, and eliminates the necessity of conventional lubricating powders, such as talc, which may contaminate the surgical procedures.

A surgical glove may be used by a medical practitioner when one or more fingers must be inserted into an opening of a patient's body. One type of self-lubricating surgical glove designed for use in vaginal and rectal examinations is disclosed in Seltzer (U.S. Pat. No. 3,911,501). The surgical glove is made of rubber and has a hollow, isolated compartment or bubble containing a lubricant mounted on the exterior tip of one of the glove finger stalls. Once the glove is on his hand, the physician squeezes his fingers together to burst the bubble, discharging lubricant onto the glove to facilitate an examination. Correspondingly, Ulbrich (U.S. Pat. No. 4,951,815) discloses a medical glove and lubricant dispensing package to assist the medical practitioner with body cavity examinations. The package consists of two sheets of protective material formed together to produce two separate compartments for sealing and encasing a surgical glove in one compartment and a supply of lubricant in the other compartment. Preceding an examination, the medical practitioner separates the two sheets of protective material, slips the surgical glove over his hand and applies the lubricant to the surgical glove.

Surgical gloves may contain more than one layer of material to protect the surgeon and patient from contamination. Schonholtz (U.S. Pat. No. 3,633,216) discloses a multi-layer, rubber surgical glove with at least one finger portion of double thickness to prevent punctures in the glove. Additionally, the multi-layer glove may contain an indicator substance, such as colored saline solution, inserted between the multi-layered areas. If a layer of the glove is ruptured, the indicator substance escapes and alerts the surgeon to discard and replace the ruptured glove.

Although traditional skin care techniques and pre-lubricated gloves are useful in many applications, they do not address various skin care problems. Traditional skin care techniques utilize exposed, messy lotions which must be re-applied. Pre-lubricated gloves do not provide any form of skin care for the user.

SUMMARY OF THE INVENTION

Accordingly, it is an object of the present invention to provide an improved skin care technique and apparatus.

It is another object to provide skin care techniques and implements that avoid exposed, messy lotions.

It is still another object to provide skin care techniques and apparel to enable continuous application of lotion to a human extremity without re-application of the lotion.

A moisturizing glove constructed according to the principles of the present invention has an inner layer having a plurality of pores, an exterior surface and an interior surface opposite the exterior surface. The interior surface is formed to create a cavity for receiving and enveloping a human extremity. A middle layer is saturated with lotion, the middle layer has a bottom surface and a top surface opposite the bottom surface. The bottom surface abuts and covers the exterior surface of the inner layer, and an exterior layer of non-porous material has a lower surface abutting and covering the top surface of the middle layer.

An alternative embodiment provides a moisturizing glove with an inner layer having a plurality of pores, an exterior surface and an interior surface opposite the exterior surface. The interior surface is formed to create a cavity having a plurality of finger stalls and a palm portion for receiving and enveloping a human extremity. A middle layer is saturated with lotion, and has a bottom surface and a top surface opposite the bottom surface. The bottom surface abuts and covers the exterior surface of the inner layer, and an exterior layer of non-porous material having a lower surface and an extrinsic surface opposite the lower surface. The lower surface abuts and covers the top surface of the middle layer.

Another embodiment provides a moisturizing glove with an inner layer having a plurality of pores, an exterior surface and an interior surface opposite the exterior surface. The interior surface is formed to create a cavity having a plurality of finger stalls and a palm portion for receiving and enveloping a human extremity. A middle layer saturated with lotion has a bottom surface and a top surface opposite the bottom surface, the bottom surface abuts and covers the exterior surface of the inner layer. An exterior layer of non-porous material has a lower surface and an extrinsic surface opposite the lower surface. The lower surface abuts and covers the top surface of the middle layer, and a temporary sealing layer of non-porous material which ruptures after the human extremity is received by the inner layer, having an outer surface and an inner surface opposite the outer surface, wherein the outer surface abuts and is formed to the bottom surface of the middle layer and the inner surface abuts and is formed to the exterior surface of the inner layer.

An additional embodiment provides a moisturizing glove with an inner layer having a plurality of pores, an exterior surface and an interior surface opposite the exterior surface, wherein the interior surface is formed to create a cavity having a plurality of finger stalls and a palm portion for receiving and enveloping a human extremity, a middle layer saturated with lotion, wherein the middle layer has a bottom surface and a top surface opposite the bottom surface, wherein the bottom surface abuts and covers the exterior surface of the inner layer, and an exterior layer of non-porous material having a lower surface, an extrinsic surface opposite the lower surface, wherein the lower surface abuts and covers the top surface of the middle layer, a temporary sealing layer of non-porous material which ruptures after the human extremity is received by the inner layer, having an outer surface and an inner surface opposite the outer surface. The outer surface abuts and is formed on the bottom surface of the middle layer and the inner surface abuts and is formed on the exterior surface of the inner layer. A protective layer has a base surface abutting and covering the extrinsic surface of the exterior layer.

Still another embodiment provides a method of moisturizing a human extremity using a moisturizing glove having a middle layer saturated with lotion formed on an inner layer having a plurality of pores and an interior surface formed to create a cavity having a plurality of finger stalls and a palm portion for receiving and enveloping the human extremity. The method contemplates inserting the human extremity into the cavity formed by the inner layer of the moisturizing glove, transferring the lotion from the middle layer through the plurality of pores of the inner layer and depositing the lotion transferred through the plurality of pores of the inner layer onto the human extremity.

A further embodiment provides a method of moisturizing a human extremity using a moisturizing glove having a middle layer saturated with lotion, formed with a non-porous temporary sealing layer that is formed on an inner layer having a plurality of pores and an interior surface formed to create a cavity having a plurality of finger stalls and a palm portion for receiving and enveloping the extremity. The method contemplates inserting the human extremity into the cavity formed by the inner layer of the moisturizing glove; rupturing the non-porous temporary sealing layer; transferring the lotion from the middle layer through the plurality of pores of the inner layer; and depositing the lotion transferred through the plurality of pores of the inner layer onto the human extremity.

Other details, objects and advantages of the invention will become apparent as the following description of certain present embodiments thereof and certain present preferred methods of practicing the same proceeds.

In the accompanying drawings, I have shown certain present preferred embodiments of the invention and have illustrated certain present preferred methods of practicing the same.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
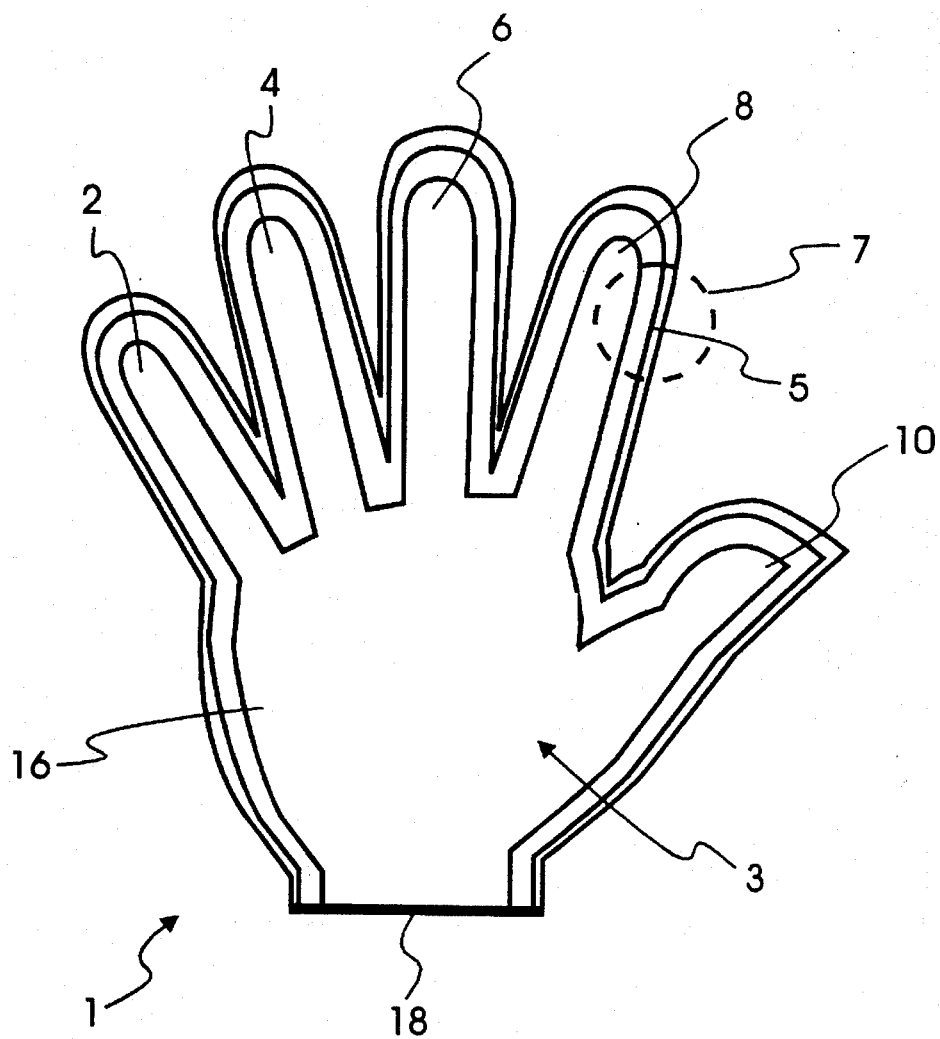
FIG. 1 is a full view diagram of the moisturizing glove of the invention.

Turning now to the drawings and referring to FIG. 1, the moisturizing glove of the invention is generally depicted at reference numeral 1. The glove is constructed of multiple layers of flexible, pliable, stretchable material 5 which form a cavity 3 for receiving and enveloping a human extremity including a hand and a foot. Cavity 3 is made up of palm portion 16 and finger stalls 2, 4, 6, 8 and 10.

Figure 2:
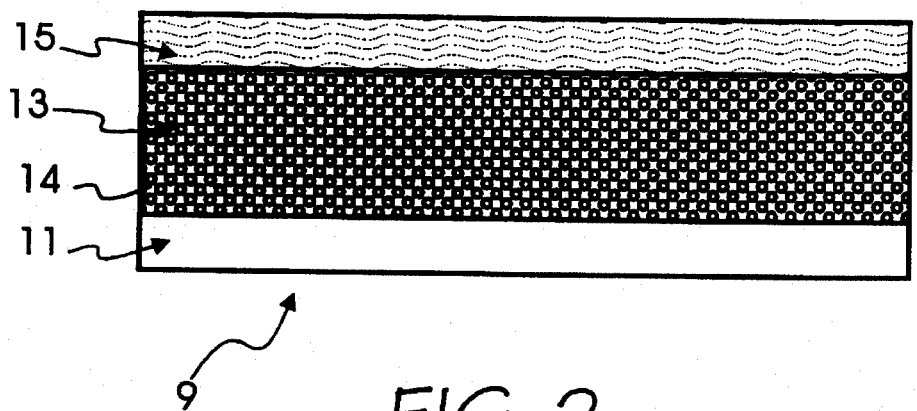
FIG. 2 is a cross-sectional diagram of a first embodiment of the moisturizing glove showing the exterior layer, middle layer and inner layer of the moisturizing glove.
Figure 8:
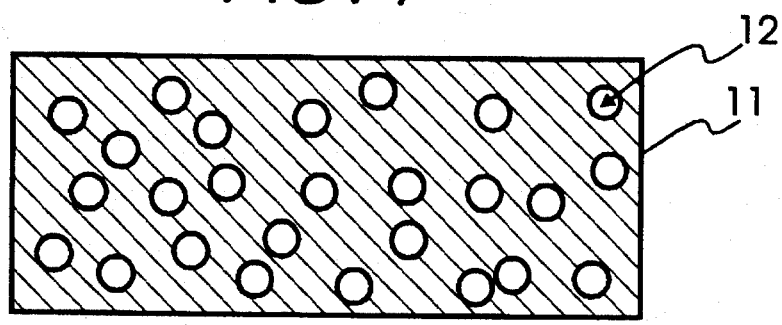
FIG. 8 is a top view of a section of the inner layer illustrating the pores of the inner layer.

FIG. 2 illustrates a first embodiment of the moisturizing glove 1. The multiple layer illustration shown generally at 9 is a cross-sectional view of the multiple layers of material of the moisturizing glove 1 taken along line 7 of FIG. 1. The first embodiment of the moisturizing glove 1 has an inner layer 11, a middle layer 13 and an exterior layer 15. The inner layer 11 may be made of a porous material, such as cotton. FIG. 8 depicts the pores 12 of inner layer 11. The middle layer 13 is saturated with lotion 14, and may consist of an absorbent, sponge-like material. The exterior layer 15 is a non-porous material, such as latex or rubber.

Figure 3:
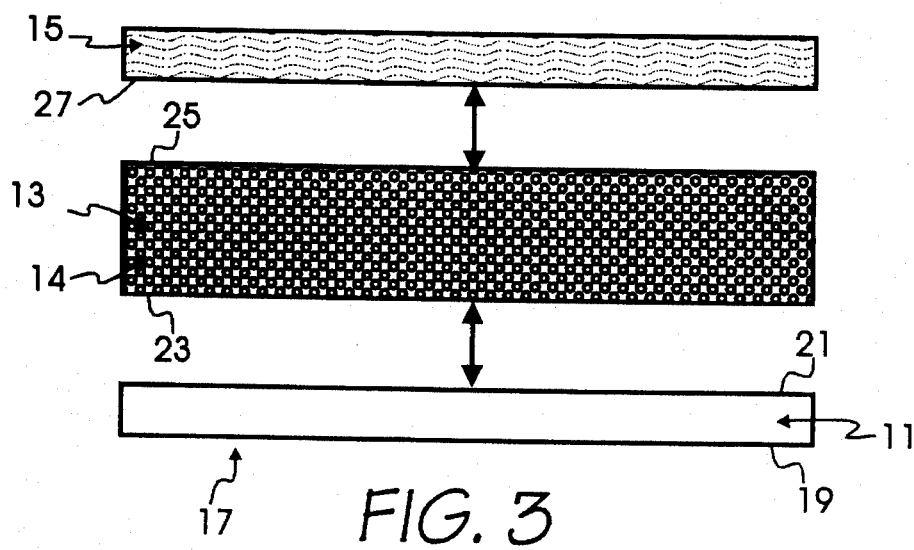
FIG. 3 is a separated view of the cross-sectional diagram of the first embodiment of the moisturizing glove shown in FIG. 2.

Turning to FIG. 3, the construction of the first embodiment of moisturizing glove 1 is shown generally at 17. The inner layer 11 of the moisturizing glove has an interior side 19 and an exterior side 21. Interior side 19 forms the cavity 3 which receives and envelopes a human extremity including a hand and a foot. Exterior side 21 is formed to and abuts the bottom side 23 of the middle layer 13. Middle layer 13 also has a top side 25 abutting and formed to the lower side 27 of the exterior layer 15.

Figure 4:
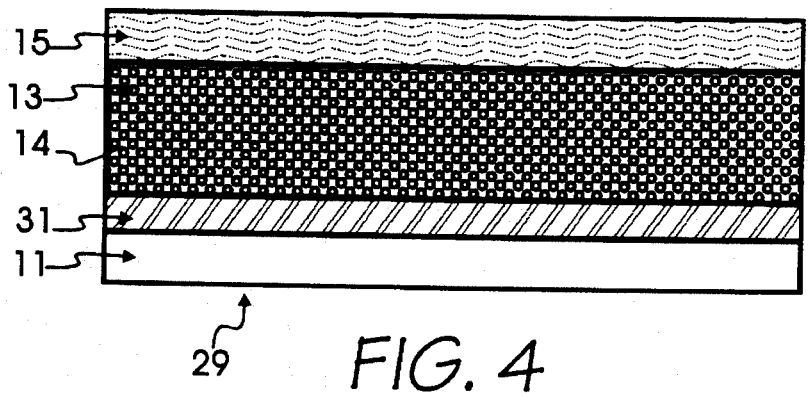
FIG. 4 is a cross-sectional diagram of a second embodiment of the moisturizing glove showing the exterior layer, middle layer, inner layer and temporary sealing layer of the moisturizing glove.

A second embodiment of the moisturizing glove 1 is illustrated by FIG. 4. The multiple layer illustration shown generally at 29 is a cross-sectional view of the multiple layers of material of the moisturizing glove 1 taken along line 7 of FIG. 1. The second embodiment of the moisturizing glove 1 has an inner layer 11, a middle layer 13, a temporary sealing layer 31 and an exterior layer 15. The inner layer 11 may be made of a porous material, such as cotton. The middle layer 13 is saturated with lotion 14, and may consist of an absorbent, sponge-like material. The temporary sealing layer 31 consists of a non-porous material which ruptures after a human extremity including a hand and a foot is inserted into moisturizing glove 1. Temporary sealing layer 31 may be made of various materials, such as a temperature sensitive material which ruptures in response to heat from a human extremity including a hand and a foot, a pressure sensitive material of multiple rubber or latex striations overlapping each other and formed to rupture in response to pressure, or a perspiration sensitive material which ruptures when encountered with perspiration. The exterior layer 15 is a non-porous material, such as latex or rubber.

Figure 5:
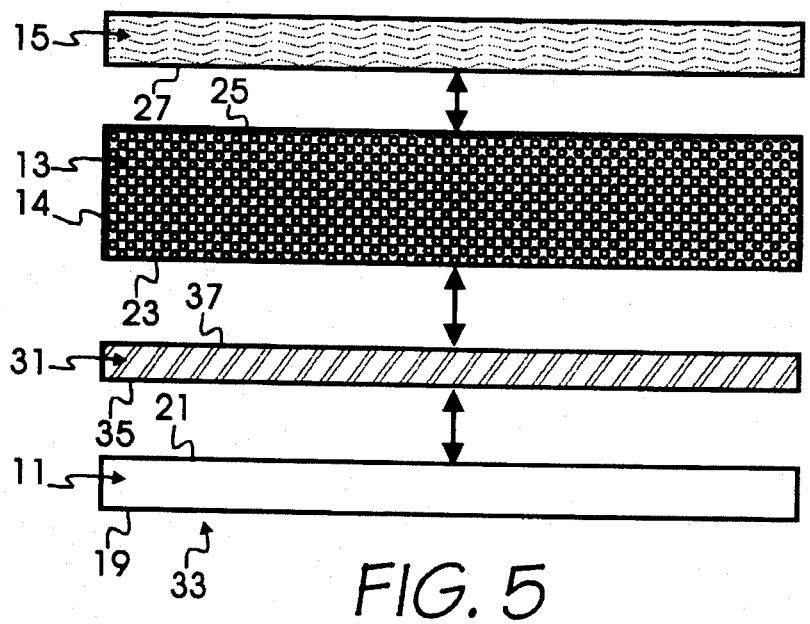
FIG. 5 is a separated view of the cross-sectional diagram of the second embodiment of the moisturizing glove shown in FIG. 4.

FIG. 5 illustrates the construction of the second embodiment of moisturizing glove 1, shown generally at 33. The inner layer 11 of the moisturizing glove has an interior side 19 and an exterior side 21. Interior side 19 forms the cavity 3 which receives and envelopes a human extremity including a hand and a foot. Exterior side 21 is formed to and abuts the inner side 35 of the temporary sealing layer 31. The outer side 37 of temporary sealing layer 31 is formed to the bottom side 23 of middle layer 13. Middle layer 13 also has a top side 25 abutting and formed to the lower side 27 of the exterior layer 15.

Figure 6:
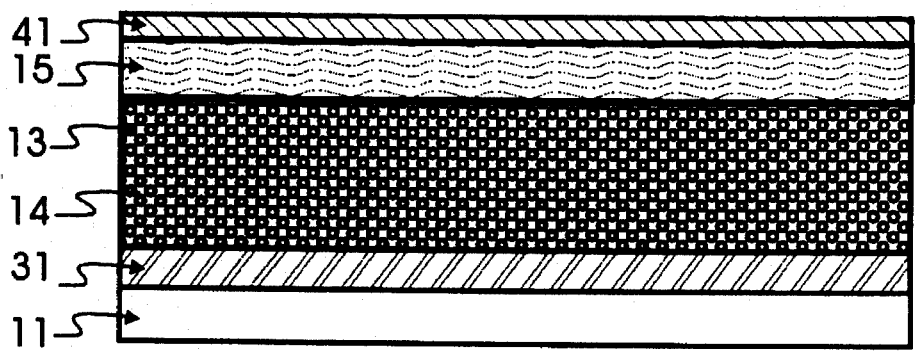
FIG. 6 is a cross-sectional diagram of a third embodiment of the moisturizing glove showing the exterior layer, middle layer, inner layer, temporary sealing layer and protective layer of the moisturizing glove.

A third embodiment of moisturizing glove 1 is illustrated in FIG. 6. The multiple layer illustration shown generally at 39 is a cross-sectional view of the multiple layers of material of the moisturizing glove 1 taken along line 7 of FIG. 1. The third embodiment of the moisturizing glove 1 has an inner layer 11, a middle layer 13, a temporary sealing layer 31, an exterior layer 15 and a protective layer 41. The inner layer 11 may be made of a porous material, such as cotton. The middle layer 13 is saturated with lotion 14, and may consist of an absorbent, sponge-like material. The temporary sealing layer 31 consists of a non-porous material which ruptures after a human extremity including a hand and a foot is inserted into moisturizing glove 1. Temporary sealing layer 31 may be made of various materials, such as a temperature sensitive material which ruptures in response to heat from a human extremity including a hand and a foot, a pressure sensitive material which ruptures in response to pressure, or a perspiration sensitive material which ruptures when encountered with perspiration. The exterior layer 15 is a non-porous material, such as latex or rubber. Protective layer 41 is preferably made of a soft, sponge-like material.

Figure 7:
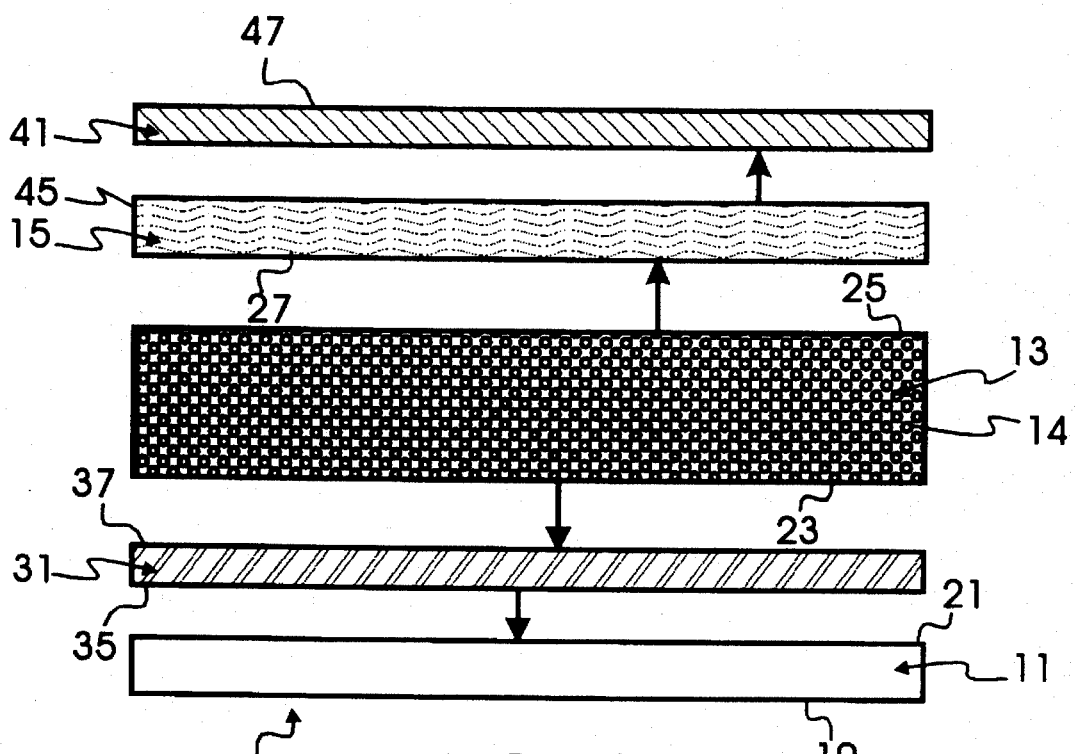
FIG. 7 is a separated view of the cross-sectional diagram of the third embodiment of the moisturizing glove shown in FIG. 6.

FIG. 7 illustrates the construction of the third embodiment of moisturizing glove 1, shown generally at 43. The inner layer 11 of the moisturizing glove has an interior side 19 and an exterior side 21. Interior side 19 forms the cavity 3 which receives and envelopes a human extremity including a hand and a foot. Exterior side 21 is formed to and abuts the inner side 35 of the temporary sealing layer 31. The outer side 37 of temporary sealing layer 31 is formed to the bottom side 23 of middle layer 13. Middle layer 13 also has a top side 25 abutting and formed to the lower side 27 of the exterior layer 15. Exterior layer 15 has an extrinsic surface 45 formed to the base surface 47 of protective layer 41.

In its intended mode of operation, the moisturizing glove 1 provides an improved skin care technique for the human hand which does not utilize exposed, messy lotions which must constantly be re-applied.

To begin the moisturizing process, a user inserts a hand into the cavity 3 formed by the inner layer 11 of the moisturizing glove 1. Finger stalls 2, 4, 6, 8 and 10 receive the fingers and thumb of the inserted hand and palm portion 16 receives the remaining portion of the inserted hand. Once the hand is inserted into the moisturizing glove 1, the non-porous temporary sealing layer 31 ruptures.

The temporary sealing layer 31 may be designed to rupture in response to various stimuli created by the inserted hand. For example, heat transferred from a hand through inner layer 11 to the temporary sealing layer 31 may cause one version of the temporary sealing layer 31 to rupture. Alternatively, pressure transferred from an inserted hand to the inner layer 11, and consequently to the temporary sealing layer 31 may cause a different version of the temporary sealing layer 31 to rupture. Finally, perspiration produced by an inserted hand which travels through the pores 12 of inner layer 11, and consequently contacts the temporary sealing layer 31 may cause a another version of the temporary sealing layer 31 to rupture once a hand is inserted into the moisturizing glove 1.

Subsequent to the rupture of the temporary sealing layer 31, the actual moisturizing process begins. Lotion 14 previously contained in the middle layer 13 by the non-porous temporary sealing layer 31 and the exterior layer 15 begins to moisturize the inserted hand after the temporary sealing layer 31 is ruptured. The lotion 14 is released from the middle layer 13, and travels through the bottom side 25 of the middle layer 13 to the exterior side 21 of the inner layer 11 of the moisturizing glove 1. Next, the lotion 14 enters the pores 12 of the inner layer 11. The lotion 14 travels through the pores 12, the interior side 19 of the inner layer 11 and is deposited on the inserted hand, thereby moisturizing the inserted hand. Consequently, the inserted hand is moisturized as long as the hand remains in the moisturizing glove 1.

During use, the moisturizing glove 1 avoids any transfer of lotion 14 to exterior objects. The exterior layer 15 provides a non-porous sealing layer which inhibits the lotion 14 from travelling through the lower side 27 of the exterior layer 15. Consequently, no lotion escapes from the moisturizing glove 1.

Additionally, the moisturizing glove i may be equipped with a protective layer 41 to provide a soft exterior and protect the exterior layer 15 from possible rupture. The protective layer 41 acts as a buffer to protect the exterior layer 15 and to provide a cushion for moisturizing glove The moisturizing glove previously described may be adapted as a moisturizing glove for moisturizing a foot.

While I have shown and described certain present preferred embodiments of the invention and have illustrated certain present preferred methods of practicing the same it is to be distinctly understood that the invention is not limited thereto but may be otherwise variously embodied and practiced within the scope of the following claims.

I claim:

1. A moisturizing glove, comprising:

an inner layer of stretchable, porous material having an exterior surface and an interior surface opposite from said exterior surface, said inner layer being perforated throughout by a continuous distribution of a plurality of discrete pores, said interior surface forming a cavity for receiving and enveloping an anatomical human member;

a quantity of a lotion;

a middle layer comprising a thickness of stretchable spongy material absorbent of said lotion extending continuously throughout said middle layer and saturated with said lotion, said quantity of lotion being distributed throughout said thickness, said middle layer having an interior surface and an exterior surface opposite and separated by said thickness from said interior surface, said interior surface of said middle layer covering said exterior surface of said inner layer and responding to stimuli of insertion of an anatomical human member into said cavity by continuously releasing said lotion to said inner layer to enable said lotion to migrate through said plurality of pores, be deposited upon and moisturize the anatomical member with said lotion; and an outer layer of stretchable, non-porous material having an interior surface abutting and covering said exterior surface of said middle layer.

2. A moisturizing glove, comprising:

an inner layer of flexible material perforated throughout by a continuous distribution of a plurality of discrete pores, said inner layer having an exterior surface and an interior surface opposite from said exterior surface, said interior surface forming a cavity having a plurality of finger stalls and a palm portion for receiving and enveloping a human extremity;

a quantity of lotion;

a middle layer of a stretchable, spongy material permeated with said lotion, said quantity of lotion being absorbed in continuous distribution throughout said material, said middle layer having an interior surface and an exterior surface opposite from said interior surface, said interior surface of said middle layer covering said exterior surface of said inner layer and responding to stimuli of insertion of said human extremity into said cavity by continuously releasing said lotion to said inner layer to enable said lotion to migrate through said plurality of pores, be deposited upon and moisturize the human extremity; and an outer layer of non-porous, stretchable material having an interior surface and an exterior surface opposite said interior surface, said interior surface of said outer layer abutting and covering said exterior surface of said middle layer.

3. A moisturizing glove as recited in claim 2, further comprising a temporary sealing layer of non-porous material perforatable upon receipt of a human extremity by said inner layer, having an outer surface and an inner surface opposite said outer surface, said outer surface of said temporary sealing layer abutting and covered by said interior surface of said middle layer and said inner surface of said temporary sealing layer abutting and covering said exterior surface of said inner layer.

4. A moisturizing glove as recited in claim 3, further comprising a protective layer having a base surface formed to and covering said exterior surface of said outer layer.

5. A moisturizing glove as recited in claim 3, said temporary sealing layer of non-porous material comprising a temperature sensitive material which ruptures in response to heat transferred by said human extremity to said temporary sealing layer after said human extremity is received by said inner layer.

6. A moisturizing glove as recited in claim 3, said temporary sealing layer of non-porous material comprising a pressure sensitive material which ruptures in response to pressure transferred by said human extremity to said temporary sealing layer after said human extremity is received by said inner layer.

7. A moisturizing glove as recited in claim 3, said temporary sealing layer of non-porous material comprising a perspiration sensitive material which ruptures in response to perspiration transferred by said human extremity to said temporary sealing layer after said human extremity is received by said inner layer.

8. A moisturizing glove as recited in claim 2, said middle layer comprised of spongy material characterized as being uniformly stretchable and uniformly absorbent of said lotion throughout said material of said middle layer.

9. A moisturizing glove as recited in claim 1, with said outer layer comprising latex.

10. A moisturizing glove as recited in claim 2, said outer layer of non-porous material comprising latex.

11. A moisturizing glove as recited in claim 2, said lotion comprising a solution selected from the group comprising a moisturizing lotion and a medicated lotion.

12. A moisturizing glove as recited in claim 1, further comprising a temporary sealing layer of non-porous material perforable upon receipt of an anatomical human member by said inner layer, said temporary sealing layer having an outer surface and an inner surface opposite said outer surface, said outer surface of said temporary sealing layer abutting and covered by said interior surface of said middle layer and said inner surface of said temporary sealing layer abutting and covering said exterior surface of said inner layer.

13. A moisturizing glove as recited in claim 1, comprising of said lotion throuout said cavity
said middle layer of stretchable material further characterized as being absorbent.

14. A moisturizing glove as recited in claim 1, further comprising a protective layer having a base surface formed to and covering an exterior surface of said outer layer.

15. A moisturizing glove as recited in claim 12, said temporary sealing layer of non-porous material comprising a temperature sensitive material susceptible to rupturing in response to heat transferred by said anatomical human member to said temporary sealing layer after said anatomical human member is received by said inner layer.

16. A moisturizing glove as recited in claim 12, said temporary sealing layer of non-porous material comprising a pressure sensitive material susceptible to rupturing in response to pressure transferred by said anatomical human member to said temporary sealing layer after said anatomical human member is received by said inner layer.

17. A moisturizing glove as recited in claim 12, said temporary sealing layer of non-porous material comprising a perspiration sensitive material susceptible to rupturing in response to perspiration transferred by said anatomical human member to said temporary sealing layer after said anatomical human member is received by said inner layer.

18. A moisturizing glove as recited in claim 2, further comprising:

said middle layer of spongy material characterized as being stretchable and absorbent of said lotion throughout said material of said middle layer.

19. A moisturizing glove, comprising:

a quantity of skin care lotion;

a first layer of an absorbent, porous, stretchable, spongy material forming an interior cavity comprised of a palm portion and a plurality of discrete finger stalls radiating outwardly from said palm portion, for receiving and enveloping an anatomical human member, said porous material accommodating release of said lotion in response to stimuli created by a presence of the anatomical human member within said cavity, said quantity of lotion being absorbed in continuous distribution throughout said spongy material prior to said presence, said first layer releasing said lotion from said spongy material to enable said lotion to be deposited upon and moisturize said anatomical human member during said presence;

an outer layer of stretchable material impermeable to said lotion, coextensively and continuously abutting and covering an outermost surface of said first layer; and porous means foamed of a porous material positioned within said cavity coextensively and continuously abutting said first layer throughout said cavity, with said porous means interposed between an innermost surface of said first layer and the anatomical human member, for responding to said presence of the anatomical human member into said cavity, by providing controlled and continuous application of said lotion from said first layer to over substantially an entire surface of the anatomical human member within said cavity.

20. A moisturizing glove, comprising:

a quantity of skin care lotion;

a first layer of an absorbent, porous, stretchable, spongy material forming an interior cavity comprised of a palm portion and a plurality of discrete finger stalls radiating outwardly from said palm portion, for receiving and enveloping an anatomical human member, said porous material accommodating release of said lotion in response to stimuli created by a presence of the anatomical human member within said cavity, said quantity of lotion being absorbed in continuous distribution throughout said spongy material prior to said presence, said first layer releasing said lotion from said spongy material to enable said lotion to be deposited upon and moisturize said anatomical human member during said presence; and an outer layer of stretchable material impermeable to said lotion, coextensively and continuously abutting and covering an outermost surface of said first layer.

21. The moisturizing glove of claim 20, with said outer layer comprising a non-porous covering of latex.

22. The moisturizing glove of claim 20, further comprised of a layer of a porous material positioned within said cavity adjoining said first layer.

* * * * *